United States Patent
Kanie et al.

(10) Patent No.: US 7,468,058 B2
(45) Date of Patent: Dec. 23, 2008

(54) SUCTION FLUID COLLECTOR FOR MEDICAL APPLICATIONS

(75) Inventors: Nobuatsu Kanie, Fukuroi (JP); Akira Itoh, Fukuroi (JP); Dai Sutoh, Fukuroi (JP)

(73) Assignee: Tyco Healthcare Group LP, Mansfield, MA (US)

( * ) Notice: Subject to any disclaimer, the term of this patent is extended or adjusted under 35 U.S.C. 154(b) by 0 days.

(21) Appl. No.: 11/682,925

(22) Filed: Mar. 7, 2007

(65) Prior Publication Data
US 2007/0219531 A1    Sep. 20, 2007

(30) Foreign Application Priority Data
Mar. 8, 2006   (JP) ............... 2006-062340

(51) Int. Cl.
*A61M 1/00* (2006.01)

(52) U.S. Cl. ............... 604/540; 604/317; 604/318; 604/320; 604/321; 604/322; 604/323; 604/324; 604/325; 604/326; 604/541; 604/542; 604/543; 604/544

(58) Field of Classification Search ........... 604/317, 604/318, 320, 321, 322, 323, 324, 325, 326, 604/540, 541, 542, 543, 544, 340
See application file for complete search history.

(56) References Cited

U.S. PATENT DOCUMENTS

| | | | | |
|---|---|---|---|---|
| 1,573,721 A | * | 2/1926 | Loeffler | 190/107 |
| 3,572,340 A | * | 3/1971 | Lloyd | 604/133 |
| 3,866,608 A | * | 2/1975 | Reynolds et al. | 604/319 |
| 4,397,643 A | * | 8/1983 | Rygiel | 604/317 |
| 4,429,693 A | | 2/1984 | Blake et al. | |
| 4,455,140 A | * | 6/1984 | Joslin | 604/317 |
| 4,492,313 A | * | 1/1985 | Touzani | 215/372 |
| 4,773,458 A | * | 9/1988 | Touzani | 220/666 |
| 5,310,068 A | * | 5/1994 | Saghri | 251/386 |

FOREIGN PATENT DOCUMENTS

| | | |
|---|---|---|
| EP | 0048164 A1 | 3/1982 |
| EP | 0 186 783 A1 | 7/1986 |
| EP | 1566188 A1 | 8/2005 |
| WO | 98/35718 | 8/1998 |

OTHER PUBLICATIONS

Extended European Search Report regarding Application No. 06026354.8-2310 dated Jul. 5, 2007.

* cited by examiner

*Primary Examiner*—Tatyana Zalukaeva
*Assistant Examiner*—Ilya Y Treyger

(57) ABSTRACT

A suction fluid collector includes a transparent reservoir made of a resilient material with an upper opening positioned on one side of a flexible suction bag with at least one transparent side. A plate part made of a resilient material is positioned on another side of the suction bag opposite said reservoir. An urging means arranged between the reservoir and the plate part provides a force tending to expand a gap between the reservoir and the plate part. A suction tube is positioned partially inside the reservoir and extends through the suction bag.

1 Claim, 5 Drawing Sheets

SUCTION FLUID COLLECTOR FOR MEDICAL APPLICATIONS

FIELD OF THE INVENTION

The present invention generally relates to a suction fluid collector.

BACKGROUND OF THE INVENTION

Conventionally, for example, body fluids, etc. (blood, exudates, etc.) are drawn out by retaining the tip of a catheter in the wound of a patient. In this case, the end of the catheter is connected to a suction fluid collector for medical use and body fluids, etc. are removed through suction by operating the suction fluid collector for medical use (for example, cf. Japanese Kokai Patent Application No. Sho 57[1982]8134). Said suction fluid collector for medical use comprises a rectangular plastic bag furnished with a tube connected to the outside and a pair of plates inside and a spring body set between the pair of plates. With this constitution, the suction force generated by the expansion of the plastic bag when the spring is changed from a contracted condition to an extended condition is utilized to suck out body fluids, etc. from the wound of a patient.

The drawback for said conventional suction fluid collector for medical use is that the amount of exudate accumulated in the plastic bag cannot be accurately verified due to the deformation of the plastic bag when the exudate discharged from the body is accumulated in the plastic bag.

SUMMARY OF THE INVENTION

In one aspect of the present invention, a suction fluid collector generally comprises a transparent reservoir made of a resilient material with an upper opening positioned on one side of a flexible suction bag with at least one transparent side. A plate part made of a resilient material is positioned on another side of the suction bag opposite the reservoir. An urging means arranged between the reservoir and the plate part provides a force tending to expand a gap between the reservoir and the plate part. A suction tube is positioned partially inside the reservoir and extends through the suction bag.

Other features will be in part apparent and in part pointed out hereinafter.

BRIEF DESCRIPTION OF THE DRAWINGS

Corresponding reference characters indicate corresponding parts throughout the drawings.

DETAILED DESCRIPTION OF THE DRAWINGS

Figure 1:
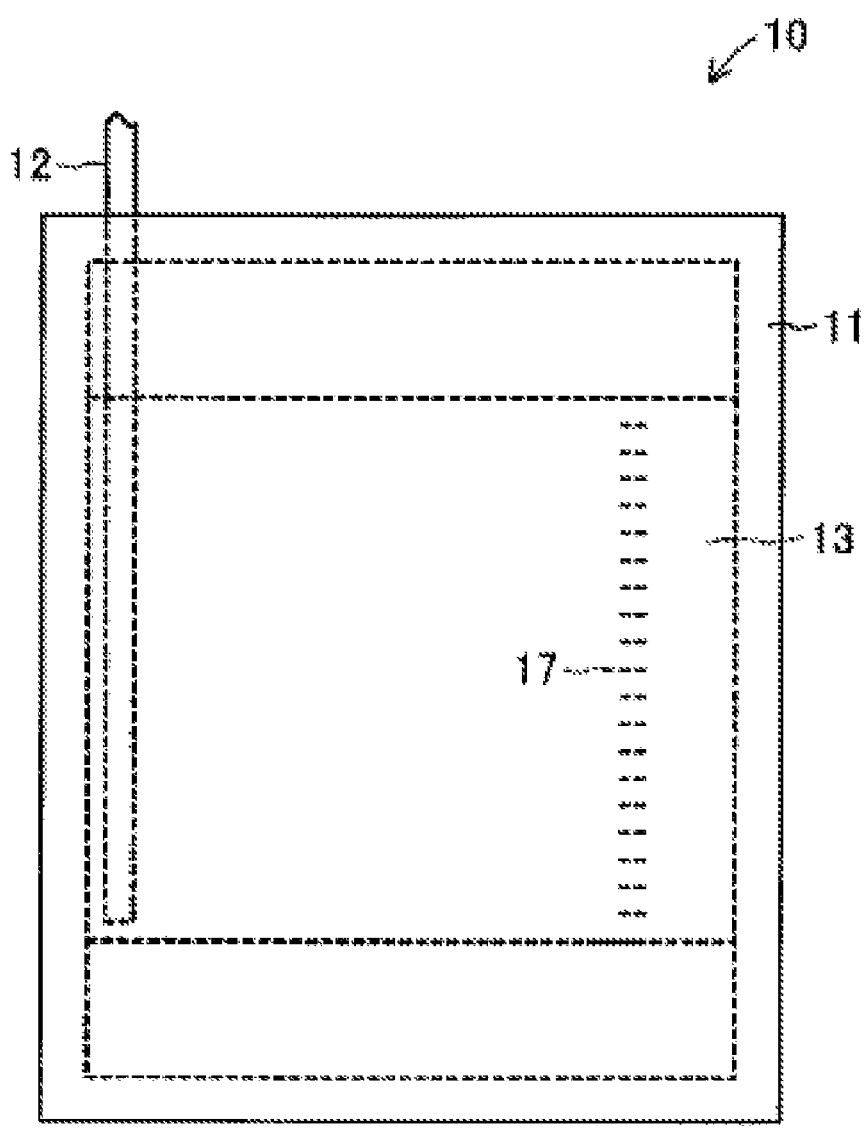
FIG. 1 is a front view of a suction fluid collector for medical application of a first embodiment of the present invention.

Next, embodiments of the suction fluid collector for medical application will be explained in detail using figures. FIG. 1 shows suction fluid collector for medical application 10 of an first embodiment. Said suction fluid collector for medical application 10 is utilized for segregating body fluids, etc. accumulated in a wound after a patient undergoes surgery by sucking the body fluids, etc. through a catheter (not shown in the figure) by connecting it to said catheter retained in the wound of the patient. Said suction fluid collector for medical application 10 comprises suction bag 11 made of a transparent soft film. Also, said suction bag 11 is formed in a square shape and suction tube 12 passes through the side of the upper part and extends from inside suction bag 11 to the outside.

Figure 2:
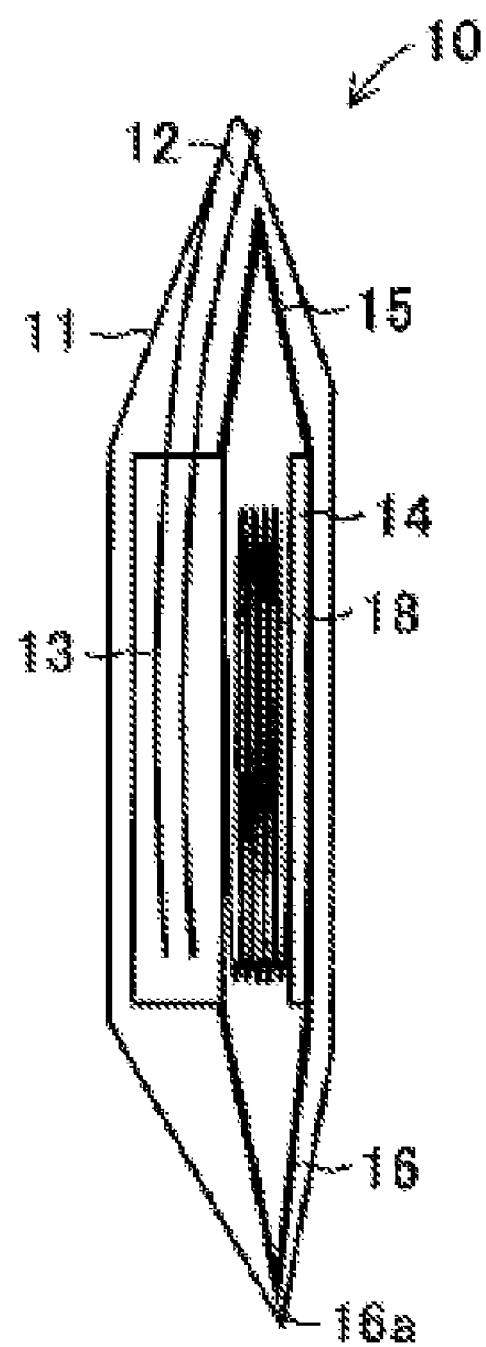
FIG. 2 is a cross sectional diagram of a suction fluid collector for medical application shown in FIG. 1.
Figure 3:
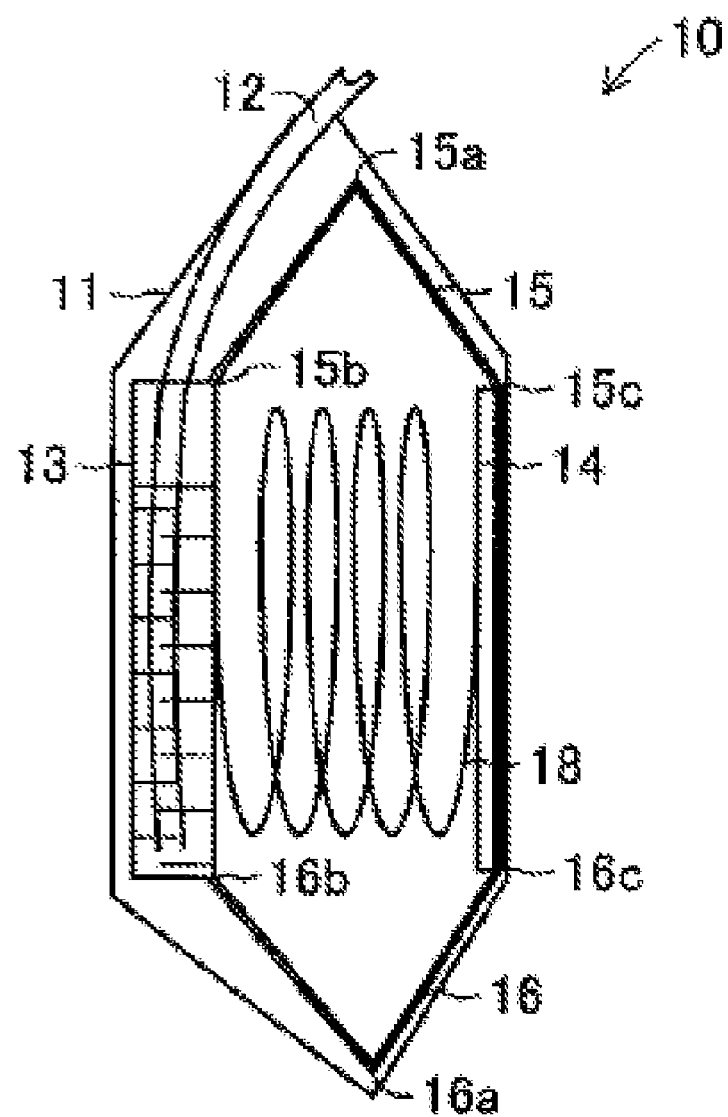
FIG. 3 is a cross sectional diagram showing the expanded condition of a suction fluid collector for medical application shown in FIG. 2.

Also, as shown in FIG. 2 and FIG. 3, reservoir 13 made of a transparent hard material is positioned on one side (surface) of suction bag 11 and square bag 14 made of a hard material is positioned on the other side (rear surface) of suction bag 11. Also, the inner side edge of the upper part of reservoir 13 and the upper edge of plate 14 are connected with connecting part 15 while the inner side edge of the lower part of reservoir 13 and the lower edge of plate 14 are connected with connecting part 16, such that reservoir 13, plate 14 and connecting parts 15 and 16 form a framework that allows a change in shape.

Reservoir 13 comprises a square container with a large rear surface area and with a smaller thickness in the direction of the rear surface and an opening on the upper part. Also, scale 17 is positioned on the surface of reservoir 13 for measuring the amount of fluid inside. Also, the base part of suction tube 12 extends through the opening of reservoir 13 to the lower side of reservoir 13. Also, connecting part 15 comprises a center part 15a, and the parts on the two sides are mutually rotateable along center part 15a. Also, connecting point 15b of connecting part 15 connected to reservoir 13 and connecting point 15c of the connecting part connected to plate 14 are thin, and reservoir 13 and connecting part 15 are mutually rotateable with connecting point 15b forming the center while plate 14 and connecting part 15 are mutually rotateable with connecting point 15c forming the center.

Also, similarly, connecting part 16 comprises a thin center part 16a, and the parts on the two sides are mutually rotateable along center part 16a. Also, connecting point 16b of connecting part 16 connected to reservoir 13 and connecting point 16c of the connecting part connected to plate 14 are thin, and reservoir 13 and connecting part 16 are mutually rotateable with connecting point 16b forming the center while plate 14 and connecting part 16 are mutually rotateable with connecting point 16c forming the center. Also, coiled spring 18 is inserted between reservoir 13 and plate 14 as a driving force for expanding the gap between reservoir 13 and plate 14. In this regard, though not shown in the figures, suction bag 11 comprises an open close part that is suitable to be opened or closed to remove reservoir 13 from the inside if necessary.

When removing body fluids, etc. from the wound of a patient using suction fluid collector for medical application 10 with said constitution, first, as shown in FIG. 2, spring 18 is contracted and the gap between reservoir 13 and plate 14 is contracted to shrink suction bag 11. The tip of suction tube 12 is then connected to the rear end of the catheter of which the front end is retained at the wound part of the patient, followed by releasing the contracting force on spring 18. By this operation, spring 18 is extended and suction bag 11 is expanded as shown in FIG. 3.

When said suction bag 11 is changed from a shrunk condition to an expanded condition, suction bag 11 generates negative pressure inside, and body fluids, etc. are sucked into reservoir 13 through the catheter and suction tube 12. In this case, suction bag 11 and reservoir 13 are transparent and scale 17 is positioned on the surface of reservoir 13 so that the amount of exudate accumulated in reservoir 13 is accurately verified. Also, when a given amount of exudate has accumulated in reservoir 13, suction tube 12 is removed from the catheter and suction bag 11 is opened and reservoir 13 inside is removed. The exudate in reservoir 13 is disposed of at a given location. Also, when conducting this operation, the catheter is closed with a clip. Reservoir 13 is then reset in suction bag 11 and said operation is repeated if necessary.

As shown above, reservoir 13 with an opening on the upper part is positioned on one side of suction bag 11, and plate 14 made of a hard material is positioned on the other side of suction bag 11 facing reservoir 13 in suction fluid collector for medical application 10 of the present invention. Also, spring 18 is arranged between reservoir 13 and plate 14. By this arrangement, when spring 18 is extended from a contracted condition, suction bag 11 is expanded and the body fluids, etc. of a patient are sucked to reservoir 13 in suction bag 11 through suction tube 12.

Also, suction bag 11 and reservoir 13 are made of transparent materials, and scale 17 is positioned on the surface of reservoir 13. Furthermore, reservoir 13 is made of a hard material. By this arrangement, reservoir 13 will not deform when exudate accumulates in reservoir 13, and suction fluid collector for medical application 10 is operated while the amount of exudate accumulated in reservoir 13 is verified.

Furthermore, the upper end part of reservoir 13 and the upper end part of plate 14 are connected by connecting part 15 with a hinge while the lower end part of reservoir 13 and the lower end part of plate 14 are connected by connecting part 16 with a hinge in such a way that reservoir 13, plate 14 and connecting parts 15 and 16 are arranged in such a framework that the gap between reservoir 13 and plate 14 is changeable. By this arrangement, the space between reservoir 13 and plate 14 will not shift and the two parts are moveable back and forward mutually with a precise relationship. As a result, suction fluid collector for medical application 10 with a durable constitution and easy operation is obtained.

Figure 4:
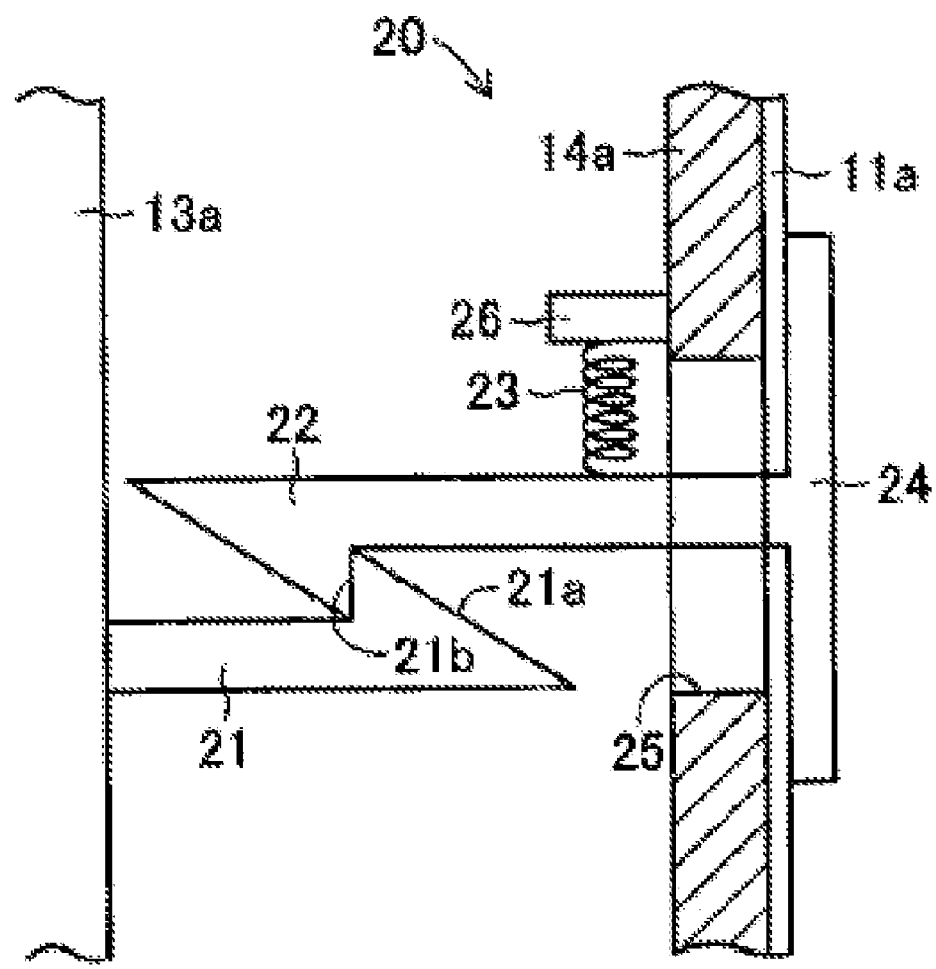
FIG. 4 is a cross sectional diagram showing the lock mechanism of the suction fluid collector for medical application of another embodiment of the present invention.
Figure 5:
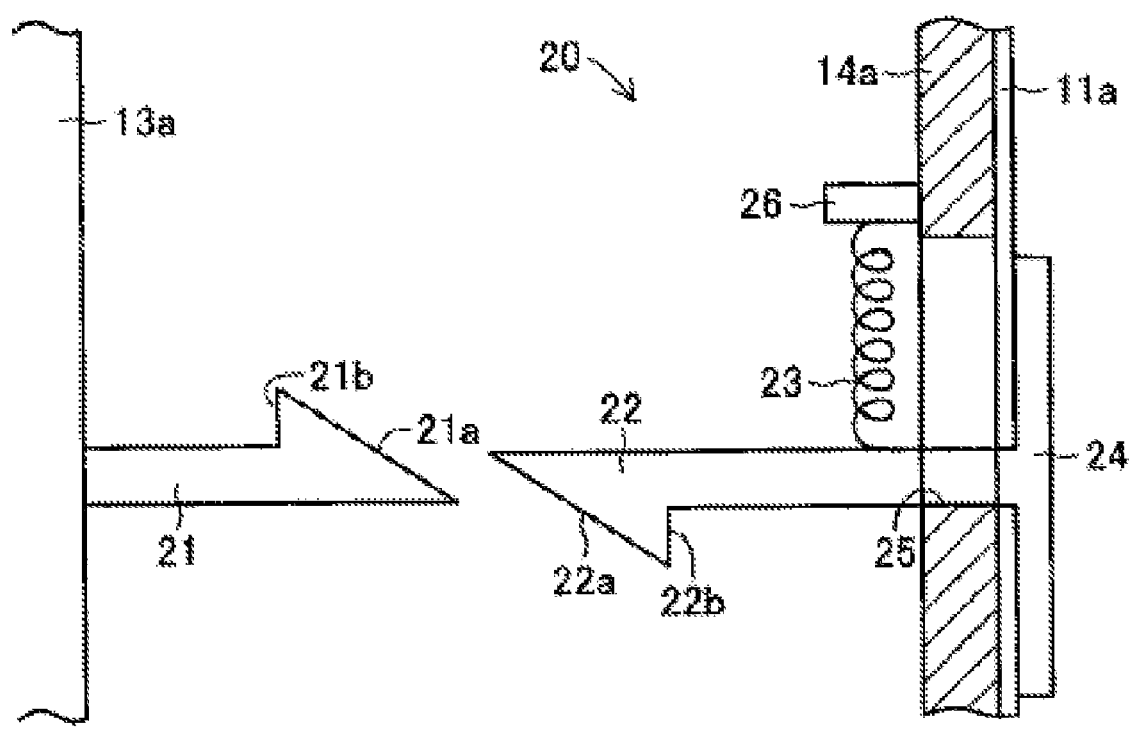
FIG. 5 is a cross sectional diagram showing the released condition of a lock mechanism of FIG. 4.

FIG. 4 and FIG. 5 show another embodiment of the suction fluid collector for medical application of the present invention, wherein a lock mechanism 20 is inserted between reservoir 13a and plate 14a. Said lock mechanism 20 comprises immobilized fitting part 21 in a wedge shape established on the inner side of reservoir 13a, mobile fitting part 22 in a wedge shape established movably on plate 14a and driving force section 23 comprising a driving spring for driving mobile fitting part 22 toward immobilized fitting part 21. Also, operating part 24 for manual handheld operation is positioned at the base part of mobile fitting part 22.

Immobilized fitting part 21 extends from the inner side of reservoir 13a toward plate 14a and comprises inclined surface 21a at the tip, and step part 21b is positioned at the rear end (the end toward the side of reservoir 13a) of inclined surface 21a. Also, mobile fitting part 22 is movably attached to plate 14a through sliding hole 25 formed in plate 14a with operating part 24 established at the base side and positioned on the outer side of suction bag 11a and the tip part extended toward reservoir 13a.

Inclined surface 22a that comes in contact with inclined surface 21a of immobilized fitting part 21 is formed at the tip of said mobile fitting part 22, and step part 22b that fits with step part 21b is formed at the base end (the end toward the side of plate 14a) of inclined surface 22a. Also, one end of driving section 23 is immobilized on installing part 26 immobilized on the inner side of plate 14a while the other end is immobilized on mobile fitting part 22 near the inner side of plate 14a.

By this arrangement, when driving force section 23 is extended fully with no force applied on driving section 23, the tip part of mobile fitting part 22 is at a position slightly higher than the tip of immobilized fitting part 21, as shown in FIG. 5. Also, by moving operating part 24 against the elastic force of driving force section 23, mobile fitting part 22 is moveable along sliding hole 25. Also, the gap between operating part 24 and suction bag 11a is sealed water tight. The constitution of other embodiments of said suction fluid collector for medical application comprising said lock mechanism 20 is the same as that of the aforementioned suction fluid collector for medical application 10.

By forming said constitution, when plate 14a is pushed toward the side of reservoir 13a from the condition shown in FIG. 5, first the tip of mobile fitting part 22 comes in contact with the tip of immobilized fitting part 21 and then inclined surface 22a of mobile fitting part 22 comes in contact with inclined surface 21a of immobilized fitting part 21 while continuing to slide. At this point, a force is applied on driving force section 23 in the contracting direction and driving force part 23 contracts. Subsequently, when the base part of inclined surface 22a passes the rear end of inclined surface 21a, step part 22b of mobile fitting part 22 fits with step part 21b of immobilized fitting part 21, resulting in the condition shown in FIG. 4.

At this point, mobile fitting part 22 is driven toward the side of immobilized fitting part 21 due to the elastic force of driving force part 23, and the fitted condition of step part 21b and step section 22b is maintained. When carrying out a suction operation, the locking condition of lock mechanism 20 is released and operating part 24 is moved against the elastic force of driving force part 23 and away from the condition in FIG. 4. By such an operation, the fitting condition of step part 21b and step part 22b is released. As a result, plate 14a moves away from reservoir 13a by the recovering force of spring 18 described earlier, and suction bag 11a is expanded.

Through such arrangement by providing a suction fluid collector for medical application with said lock mechanism 20, the operation of a suction fluid collector for medical application is simplified because the suction fluid collector for medical application is first set in a contracted condition by lock mechanism 20, and when carrying out a suction operation, the locking condition is released through the operation of operating part 24 serving as a lock release mechanism, and suction bag 11a is expanded. Also, when the suction fluid collector for medical application is not in use, lock mechanism 20 is set in the locking condition and the suction fluid collector for medical application is contracted, thus making storage very easy.

Also, the suction fluid collector for medical application of the present invention is not limited to the aforementioned application examples and is practiceable with appropriate changes. For example, suction bags 11 and 11a were made of a transparent material in the aforementioned embodiments, but as long as the surface of suction bag 11 or 11a in contact with reservoir 13 or 13a is transparent, the other parts may be opaque. Also, scale 17 was positioned on the surface of reservoir 13 and 13a in the aforementioned embodiments, but said scale may be omitted. In such a case, the amount of liquid is visually estimated because reservoir 13 and 13a are made of a hard material and deformation will not occur.

Also, in the aforementioned embodiments, spring 18 in a coiled shape is utilized as the driving force section, but other springs such as a leaf spring may be utilized in place of spring 18, and materials other than springs are suitable to be utilized. Materials that contract and expand or materials that are bent by certain operations are suitable to be utilized as said materials other than springs. Furthermore, parts such as the lock mechanism, etc. other than those constituting the suction fluid collector for medical applications are suitable to be appropriately changed in practice.

One advantage of the above-described embodiment(s) lies in providing a suction fluid collector for medical application such that the amount of exudate accumulated in the plastic bag can be accurately verified.

In at least one of the above-described embodiments, the suction fluid collector for medical application may achieve the aforementioned advantage through a transparent reservoir made of a hard material with an opening on the upper part is positioned on one side of a flexible bag part with at least one transparent side, and a plate part of a hard material is positioned on the other side of said bag part opposite said reservoir, and a driving force section is inserted between said reservoir and said plate part for providing a force to expand the gap between said reservoir and said plate part, and the base part of a suction tube that passes through said bag part and extends to the outside of said bag part is positioned inside said reservoir.

In at least one above-described embodiment, a feature is a reservoir on one side of a bag part, and a hard plate is positioned on the other side of said bag part opposite said reservoir. Also, a spring part is inserted between the reservoir and the plate. With this arrangement, the bag part is expanded and the body fluids, etc. are sucked into the bag through a suction tube when the gap between the reservoir and the plate is expanded from a condition of a shrunk gap between the reservoir and the plate by operating the driving force section. At this point, the inner side of the bag and the inner side of the reservoir are at approximately the same negative pressure because of an opening at the upper part of the reservoir.

By this arrangement, body fluids, etc. sucked into the suction tube enter into the reservoir through the base part of the suction tube. Also, in at least one embodiment, the suction fluid collector for medical application comprises a reservoir made of a transparent hard material for accumulating exudate released from the body and a bag part with a flexible surface and with at least the surface in contact with the surface of the reservoir being transparent. With this arrangement, the reservoir will not deform when exudate accumulates in the reservoir and the suction fluid collector for medical application is operateable while the amount of exudate accumulated in the reservoir is verified. In this regard, the opening of the upper part of the reservoir extends over the entire upper part or over a section of the upper part.

Also, another feature of at least one of the embodiments of the suction fluid collector for medical application a driving force section is a spring. According to this arrangement, when the contracting force of the spring is released from a contracted condition of the spring, the bag part is expanded and the body fluids, etc. of the patient are sucked into the bag part through the suction tube. In this arrangement, a driving force section is easily produced with a simple structure.

Also, another feature of at least one of the embodiments of the suction fluid collector for medical application is a lock mechanism for maintaining the contracted condition of the gap between the reservoir and the plate part by contracting the spring, and a lock release mechanism for releasing the lock mechanism. According to this arrangement, first the suction fluid collector for medical application is set at a contracted condition by the lock mechanism and the locked condition is released by releasing the lock mechanism when conducting suction, which expands the suction fluid collector for medical application, and thus operation of the suction fluid collector for medical application is easily accomplished. Also, storage is easy because the suction fluid collector for medical application is suitable to be set in a contracted condition when it is not in use.

Another feature of at least one of the embodiments of the suction fluid collector for medical application is that the reservoir comprises on the surface a scale for measuring the amount of liquid in the reservoir which is in contact with one side of the bag part. By this arrangement, the amount of exudate accumulated in the reservoir is measured accurately and not just by visual estimation.

Still another feature of at least one of the embodiments of the suction fluid collector for medical application is that the upper end of the reservoir and the upper end of the plate and the lower end of the reservoir and the lower end of the plate part are connected by hinges, respectively, in such a way that the two sides can rotate around the center, and the reservoir and the plate and the two connecting parts are arranged in such a framework that the gap between the reservoir and the plate is changeable. By this arrangement, the reservoir and the plate are suitable to move back and forward mutually with precise positional relationship without deviation from the direction parallel to the gap between the reservoir and the part. Also, by this arrangement, the suction fluid collector for medical application is formed with a solid constitution while the operation can be easily conducted.

When introducing elements of the present invention or the preferred embodiments thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A suction fluid collector comprising
transparent reservoir made of a hard material with an upper opening positioned on one side of a flexible suction bag with at least one transparent side,
a plate part made of a hard material positioned on another side of said suction bag opposite said reservoir,
urging means arranged between said reservoir and said plate part for providing a force tending to expand a gap between said reservoir and said plate part, and
a suction tube positioned partially inside said reservoir and extending through said suction bag,
wherein an upper end part of said reservoir and an upper end part of said plate part and a lower end part of said reservoir and a lower end part of said plate part are connected by respective connecting parts, and
wherein each connecting part comprises two sides mutually rotateable around a hinge formed of a hard material.

* * * * *